United States Patent
Samant et al.

(10) Patent No.: US 12,208,077 B2
(45) Date of Patent: Jan. 28, 2025

(54) SYNERGISTIC COMPOSITION FOR POTENTIATING STABILIZED ATP

(71) Applicant: CELAGENEX RESEARCH (INDIA) PVT. LTD., Maharashtra (IN)

(72) Inventors: Rajaram Samant, Thane West (IN); Rajendra Prasad Tongra, Jaipur (IN)

(73) Assignee: CELAGENEX RESEARCH (INDIA) PVT. LTD., Thane (IN)

( * ) Notice: Subject to any disclaimer, the term of this patent is extended or adjusted under 35 U.S.C. 154(b) by 279 days.

(21) Appl. No.: 17/714,723

(22) Filed: Apr. 6, 2022

(65) Prior Publication Data

US 2022/0313644 A1 Oct. 6, 2022

(30) Foreign Application Priority Data

Apr. 6, 2021 (IN) .............................. 202121016160

(51) Int. Cl.
*A61K 31/221* (2006.01)
*A61K 31/185* (2006.01)
*A61P 3/00* (2006.01)

(52) U.S. Cl.
CPC .......... *A61K 31/221* (2013.01); *A61K 31/185* (2013.01); *A61P 3/00* (2018.01)

(58) Field of Classification Search
CPC ........ A61K 31/185; A61K 31/221; A61P 3/00
See application file for complete search history.

(56) References Cited

U.S. PATENT DOCUMENTS

| 4,415,588 | A | 11/1983 | Cavazza |
| 6,245,378 | B1 | 6/2001 | Cavazza |
| 6,602,512 | B1 | 8/2003 | Cavazza |
| 7,060,295 | B2 | 6/2006 | Richardson |
| 8,518,455 | B2 | 8/2013 | Pietro |
| 10,130,602 | B2 | 11/2018 | Williams |
| 2005/0249713 | A1 | 11/2005 | Gaetani |

FOREIGN PATENT DOCUMENTS

| JP | 2001517085 A | 10/2001 |
| WO | 1998043499 A2 | 10/1998 |
| WO | 2000011968 A1 | 3/2000 |

OTHER PUBLICATIONS

James Heffley, "Magnesium taurate has considerable potential as a nutritional supplement, since both magnesium and taurine supplements improve a number of health conditions", published online Jan. 27, 2006. the whole document.

(Continued)

*Primary Examiner* — Savitha M Rao
(74) *Attorney, Agent, or Firm* — Maschoff Brennan

(57) ABSTRACT

The present invention disclosed herein relates to a synergistic composition for potentiating stabilized ATP. Particularly, the invention provides the synergistic composition for improving cellular energy in a subject in need thereof. More particularly, the invention relates to compositions comprising synergistic combination therapeutically active ALCAR and MgAT which are present in the weight ratio of 1:0.002 to 1:1, along with pharmaceutically acceptable excipients. Further, the present composition is useful for improving tiredness, fatigue, cognition, memory, increase mental alertness, concentration, endurance, boost energy levels and wakefulness. It also useful for treating depression, anxiety related symptoms.

10 Claims, 1 Drawing Sheet

(56) References Cited

OTHER PUBLICATIONS

Fassin, M., Danhier, P., & Ris, L. (2020). Effect of oral administration of Magnesium NAcetyltaurinate on synaptic plasticity in rodents. Magnesium Research, 33(4), 106-113.

Dane, H. (2017). Overcome Adrenal Fatigue: Regain Your Health & Energy.

Hosgorler, F., Koc, B., Kizildag, S., Canpolat, S., Argon, A., Karakilic, A., . . . & Uysal Harzadin, N. A. Z. A. N. (2020). Magnesium acetyl taurate prevents tissue damage and deterioration of prosocial behavior related with vasopressin levels in traumatic brain injured rats. Turkish Neurosurgery.

International Search Report dated Jul. 14, 2022 as received in application No. PCT/IN2022/050335.

Indian Examination Report dated Apr. 26, 2022 as received in application No. 202121016160.

Myhill, Booth, & Howard, 2009 Chronic fatigue syndrome and mitochondrial dysfunction.

Eur J Clin Pharmacol. 2000;56:49-55 Pharmacokinetics of intravenous ATP in cancer patients.

J Int Soc Sports Nutr. 2012; 9: 16 "Adenosine 5'-triphosphate (ATP) supplements are not orally bioavailable: a randomized, placebo-controlled cross-over trial in healthy humans".

Antonio Gnoni et al. molecules 2020, 25, 182 "Carnitine in Human Muscle Bioenergetics: Can Carnitine Supplementation Improve Physical Exercisec".

Tomassini et al., "Comparison of the effects of acetyl L-carnitine and amantadine for the treatment of fatigue in multiple sclerosis: results of a pilot, randomised, double-blind, crossover trial" Journal of the Neurological Sciences 218 (2004) 103-108.

Am J Clin Nutr. Apr. 2011, 93(4):799-808 "Oral acetyl-L-carnitine therapy reduces fatigue in overt hepatic encephalopathy: a randomized, double-blind, placebo-controlled study".

Delhi psychiatry journal vol. 15 No. 1, Apr. 2012.

Dyn Med. 2006; 5: 1 "Oxygen cost of dynamic or isometric exercise relative to recruited muscle mass".

Nutritional Outlook vol. 21 No. 7, Oct. 3, 2018.

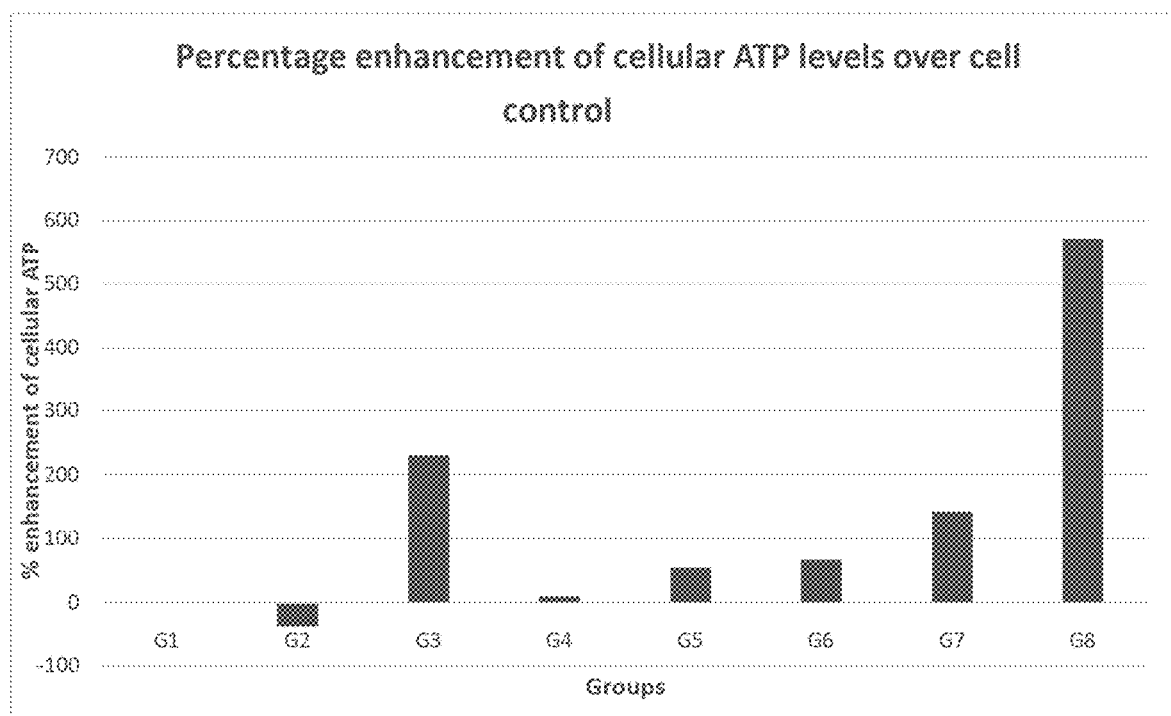

SYNERGISTIC COMPOSITION FOR POTENTIATING STABILIZED ATP

TECHNICAL FIELD

The present invention relates to synergistic compositions for potentiating stabilized ATP. Particularly, the invention provides synergistic compositions for improving cellular ATP level in a subject in need thereof.

More particularly, the invention relates to compositions comprising synergistic combination of acetyl-l-carnitine (ALCAR) and magnesium acetyl taurate (MgAT) along with pharmaceutically acceptable excipients.

Further, the present composition is useful for improving tiredness, fatigue, weakness, cognition, memory, increase mental alertness, concentration, endurance, boost energy levels and wakefulness, also useful in treatment of depression, anxiety related symptoms.

BACKGROUND

Adenosine triphosphate (ATP) is an organic compound that gives energy to run many processes in living cells of the human body. ATP is often referred to as the "molecular unit of currency" of intracellular energy transfer. In view of the structure, ATP is classified as a nucleoside triphosphate, which indicates that it consists of three components: a nitrogenous base (adenine), the sugar ribose, and the triphosphate.

Adenosine triphosphate (ATP) is the biochemical way to store and use energy. It utilizes the chemical energy found in food molecules and then releases it to fuel the work in the cell. The food is digested into small subunits of macronutrients which all converted to a glucose that to be converted to ATP.

Carbohydrates, such as glycogen, and fats are storage molecule for chemical energy; When energy is needed by the cell, it is converted from storage molecules into ATP. ATP then serves as a shuttle, delivering energy to places within the cell where energy-consuming activities are taking place Although cells continuously break down ATP to obtain energy, ATP also is constantly being synthesized from ADP and phosphate through the processes of cellular respiration. Most of the ATP in cells is produced by the enzyme ATP synthase, which converts ADP and phosphate to ATP.

There are numerous disorders or diseases associated with ATP depletion such as gene-associated to gene-non-associated disorders, age-related diseases, neurodegenerative, neuromuscular, cardiovascular, diabetic diseases, neurocognitive disorders and cancer. Particularly, there are common major disorders such as tiredness, fatigue, weakness, cognition, memory, mental alertness, concentration, endurance, energy levels and wakefulness are also associated with ATP depletion.

In most cases, such as, allergic rhinitis, anemia, depression, fibromyalgia, chronic kidney disease, liver disease, lung disease (COPD), a bacterial or viral infection, or some other health condition are led to causes fatigue due to ATP depletion.

ATP is generated by non-oxidative (substrate level phosphorylation, "anaerobic") and oxidative (oxidative phosphorylation, "aerobic") metabolic processes. Most of the health disorders often develop when substrates for ATP generation are depleted and/or when metabolic by-products accumulate in contracting muscle and the blood.

Mitochondria produce 90% of body energy. Mitochondrial impairment causes several energy deficiency disorders. The impairment of mitochondria causes a decline of cellular energy production and an advance in ageing (ageing more rapidly).

For many people, energy deficiency is caused by a combination of lifestyle, social, psychological, and general well-being issues rather than an underlying medical condition.

Particular and adequate treatment for cellular energy improvement has proven challenging, and it is often overlooked by healthcare providers due to its diagnostically non-specific nature.

Some potential contributors for energy impairment include dysfunctions in the mitochondrial structure, mitochondrial function, mitochondrial enzymes and oxidative/nitrosative stress), mitochondrial energy metabolism (ATP production and fatty acid metabolism), impaired immune response, genetics, oxidative stress, ROS production, cellular (energy) decline, ATP depletion, exposure to drugs and other xenobiotics, excessive sugar creates AGEs (Advanced glycation end products), ageing, use of a respiratory chain inhibitor-broad-spectrum insecticide, piscicide, and pesticide, exercise and metabolism and like thereof.

Mitochondria is a major source of energy for the body because it produces ATP (adenosine triphosphate), but when there are dysfunctional mitochondria, ATP cannot be produced meaning that there is a higher demand for ATP in the body than can be produced. Researchers have studied the relationship between mitochondrial dysfunction and the severity of chronic fatigue syndrome (CFS) and have found that there is a correlation between the severity of CFS and mitochondrial dysfunction (Myhill, Booth, & Howard, 2009). The "ATP profile" test is a powerful diagnostic tool and can differentiate patients who have fatigue and other symptoms which is a result of energy wastage by stress and psychological factors from those who have insufficient energy due to cellular respiration dysfunction.

It has been reported that the half-life of infused ATP is less than one second. ATP is rapidly taken up and stored by erythrocytes. This rapid uptake by erythrocytes is central to its role in affecting blood flow and oxygen delivery to oxygen-depleted tissue.

Further it is reported that ATP is bioavailable after intravenous administration in humans [*Eur J Clin Pharmacol.* 2000; 56:49-55]. ATP concentrations in erythrocytes increased in a dose-dependent manner by ~60% after 24 h of continuous infusion.

ATP supplements given by injection can cause breathing problems and chest pain, particularly when given at high doses. Headache, heart pounding, low blood pressure, nausea, sweating, flushing, lightheadedness, sleep problems, coughing, and anxiety can also occur. The oral bioavailability of an ATP nutritional supplement is higher, moreover when the ATP is administered as a single dose that has high enough to enable its detection in whole blood. [*J Int Soc Sports Nutr.* 2012; 9:16].

However, there are several limitations to produce more bioavailable oral dosage form of ATP. ATP is stable in the pH range of 7-9, but quickly decompose in acidic conditions; as a result, ATP analysis cannot be used in monitoring acidic processes.

Therefore, acid-resistant enteric coating of the multiparticulate supplement need to be used to prevent the degradation of ATP in the acidic environment of the stomach. Most of ATP dosage are formulated in extended-release pellets which is quite expensive and complicated technique. For oral administration higher dosage are need which ranges from 400 mg to 5000 mg per day. It is also observed that on oral administration ATP get degraded to uric acid where high uric acid levels may eventually lead to permanent bone, joint and tissue damage, kidney disease and heart disease.

Hence there is need to find out, cost effective, feasible, therapeutic approach that improves mitochondrial function by enhancing cellular ATP production without any severe side effect. The availability of fatty acids for oxidation as early as possible in exercise will allow the use of both fuels (fatty acids and glucose) for a longer period. Since it appears that fatigue occurs when carbohydrate reserves are depleted, reduction in the rate of glucose utilization by the oxidation of fatty acids is obviously beneficial.

Fatty acids oxidation is an important source of energy production in mammals. During periods of fasting, fatty acids turn into the predominant substrate for energy production via oxidation in the liver, cardiac muscle, and skeletal muscle. The brain does not directly use fatty acids for oxidative metabolism but utilizes ketone bodies derived from acetyl-CoA and acetoacetyl-CoA produced by β-oxidation of fatty acids in the liver.

Mitochondrial fatty acid oxidation represents an important energy source for muscle metabolism particularly during physical exercise. However, especially during high-intensity exercise, this process seems to be limited by the mitochondrial availability of free L-carnitine. Hence, fatty acid oxidation rapidly declines, increasing exercise intensity from moderate to high. Considering the important role of fatty acids in muscle bioenergetics, and the limiting effect of free carnitine in fatty acid oxidation during endurance exercise, L-carnitine supplementation has been hypothesized to improve exercise performance [Antonio Gnoni et. al. *molecules* 2020, 25, 182].

In view of above, the inventors of the present invention have observed that acetylated form of L-carnitine is more potent source of energy from fat than L-carnitine.

In human body, acetyl-L-carnitine is made from L-carnitine. L-carnitine is a derivative of an amino acid. Acetyl-L-carnitine helps the body to produce energy. It is important for heart and brain function, muscle movement, and many other body processes.

Acetyl-L-carnitine (ALCAR) is an endogenous metabolic intermediate that facilitates the influx and efflux of acetyl groups across the mitochondrial inner membrane.

L-carnitine plays a critical role in the production of energy from long-chain fatty acids. In addition, it increases the activity of certain nerve cells in the central nervous system.

A small study found that acetyl-L-carnitine works better than certain medications, such as amantadine, used to treat fatigue.

U.S. Pat. No. 10,130,602B2 discloses non-therapeutic use of L-carnitine, a salt of L-carnitine, a derivative of L-carnitine and/or a salt of a derivative of L-carnitine for reducing or preventing mental fatigue and/or for improving cognitive function in a non-elderly animal.

The management of fatigue is a complex and difficult task because multiple factors may contribute to produce this symptom. Several different medications are used to manage fatigue including amantadine, pemoline, aminopyridines and modafinil. The medication most widely used is amantadine. Among the known medications, ALCAR is better tolerated and more effective than amantadine for the treatment of MS-related fatigue [*Journal of the Neurological Sciences* 218 (2004) 103-108].

U.S. Pat. No. 8,518,455B2 describes dietary supplement enhancing the muscular energy metabolism, comprising an alkanoyl carnitine and ribose.

Patients with hepatic encephalopathy (HE) treated with ALCAR showed a decrease in the severity of both mental and physical fatigue and an increase in physical activity [*Am J Clin Nutr.* 2011 April; 93 (4): 799-808].

U.S. Pat. No. 4,415,588A describes that acetyl carnitine, particularly L-acetyl carnitine, shows immunomodulating activity.

U.S. Pat. No. 6,602,512B1 discloses combination of at least one carnitine with 1-(2-hydroxyethyl)-1-methylguanidine-O-phosphate for treating muscular energetic deficiencies, asthenia, muscle fatigue, heart fatigue, post-infarct heart conditions or enhancing sporting performances.

WO1998043499A2 nutritional supplement for facilitating the adaptation of skeletal muscle in individuals undergoing programs of strenuous exercise and counteracting defatigation and weariness in asthenic individuals is disclosed, which comprises a combination of L-carnitine, acetyl L-carnitine and propionyl L-carnitine as basic active ingredients.

Further, ALCAR has a neuromodulatory effect on neuronal cholinergic and GABAergic neurons. Chronic administration of ALCAR in experimental animal showed facilitation in the number and density of synapses. ALCAR increases choline uptake into nerve terminals, which would increase acetylcholine synthesis [*Delhi psychiatry journal* Vol. 15 No. 1, April 2012].

L-carnitine is actively transported to the brain through the blood-brain barrier by the organic cation transporter (OCTN2) and accumulates in neural cells especially as acetyl-carnitine. It has important role in the metabolism of lipids, is also a potent antioxidant (free radical scavenger) and thus protects brain tissues against oxidative damage.

However, it is reported that free ATP needs stabilization to get converted into energy. ATP (adenosine triphosphate), the main source of energy in cells, must be bound to a magnesium ion to be biologically active. In general, $Mg^{2+}$ interacts with substrates through inner sphere coordination, stabilising anions, or reactive intermediates, also including binding to ATP and activating the molecule to nucleophilic attack.

ATP is an important molecule in metabolism as it holds a lot of energy which is used in many metabolic processes. ATP has negatively charged groups that allow it to chelate metals. Usually, Mg2+ stabilizes it. ATP is made unstable by the three adjacent negative charges in its phosphate tail. ATP is an unstable molecule which hydrolyzes to ADP and inorganic phosphate and the high energy of this molecule comes from the two high-energy phosphate bonds which needs magnesium Magnesium is an essential cofactor in several cell processes. Most ATP in cells is bound to $Mg^{2+}$ since $MgATP^{2-}$ is the active species in enzyme binding and the energy producing form in active transport and muscular contraction. Therefore, any alteration in free $Mg^{2+}$ could have significant consequences in muscle metabolism. Evidence for changes in intracellular magnesium has been reported in several diseases like free $Mg^{2+}$ impairment in the skeletal muscle of patients with disorders of glycolytic metabolism [*Dyn Med.* 2006; 5:1].

In general, $Mg^{2+}$ interacts with substrates through inner sphere coordination, stabilising anions including binding to ATP and activating the molecule for energy release.

Additionally, magnesium plays a fundamental role in mitochondrial energy production. Over one-third of total cellular magnesium is found in the mitochondria and is complexed together with adenosine triphosphate (ATP) and as a component of membranes. Magnesium is, therefore, critical for basic mitochondrial functions, including the production of stabilized ATP, and confers a protective role to skeletal muscle mitochondria.

Magnesium intake, on the other hand, has repeatedly been found to reduce systemic inflammation, including significant reductions in the cytokine IL-6 and C-reactive protein (CRP) levels, two markers of inflammation. [*Nutritional Outlook* Vol. 21 No. 7, Oct. 3, 2018].

In view of foregoing literature, the inventors have found that to improve cellular energy enrichment of Mg-ATP seems to be a crucial factor and with rigorous experiments the inventors have developed novel, cost effective and bioactive ingredient based composition that enhance the stabilized ATP production by facilitating fatty acid metabolism and concomitantly enhancing intracellular free $Mg^{2+}$ concentration in synergistic manner.

OBJECTIVE OF THE INVENTION

The primary objective of the invention is to provide compositions for ameliorating cellular energy.

Another objective of the invention is to provide bioavailable, safe, non-toxic, cost-effective, anti-fatigue composition.

Another objective of the invention is to provide composition for improving cognitive and physical fatigue in a subject in need thereof.

Further, an objective of the invention is to provide synergistic combination of therapeutically active acetyl donor and bioavailable magnesium salt for improving cellular energy levels.

Another objective of the invention is to provide therapeutic composition for treating decline in ATP-related conditions through site specific action with no side effects.

SUMMARY OF THE INVENTION

To meet the above objectives, the inventors of the present invention carried out thorough experiments to establish significant effect of the active ingredients or minerals or chemical element or amino acid derivative or nutrients present in the composition for treating tiredness or weakness, in a subject in need thereof in safer way.

In an aspect, the invention relates to compositions comprising therapeutically active agents along with pharmaceutically acceptable carriers for treating mental and physical fatigue conditions.

In another aspect, the invention relates to compositions comprising synergistic combination of bioactive ingredients, present in specific weight ratio to enhance cellular stabilized Mg-ATP.

In a particular aspect, the present invention provides composition for combating fatigue comprising specific combination of ALCAR and MgAT; wherein the ALCAR improves the fatty acid metabolism and activates acetyl COA as a precursor for Kreb's cycle and acetylcholine, where MgAT provides intracellular free $Mg^{2+}$ for ATP stabilization.

In another aspect, the present invention provides synergistic nutritional compositions for potentiating stabilized ATP comprising administration of effective dose of exogenous combination of ALCAR and MgAT.

In yet another aspect, the invention relates to synergistic compositions comprising combination of ALCAR which is present in the range of 1-1000 mg and MgAT which is present in the range of 1-1000 mg, wherein elemental $Mg^{2+}$ present in the range of 1-250 mg along with pharmaceutically acceptable excipients/carriers.

In yet one more aspect, the invention discloses the synergistic composition useful to improve memory, increase mental alertness, concentration, boost energy levels and wakefulness chronic tiredness, sleepiness, endurance, stamina, physical strength, poor concentration, hallucinations to the situation at hand, low motivation, depression and grief, cognitive fatigue, mild, moderate or severe brain injury, sexual exhaustion, mental exhaustion, chronic fatigue syndrome, "brain fog", poor short-term memory: dementia, Alzheimer's disease, diabetes, stroke, heart disease, impaired decision-making and judgments, and cancer.

Abbreviations:
MgAT: Magnesium acetyl taurate
ALCAR: Acetyl-L-carnitine
MCI: Mild cognitive impairment
AD: Alzheimer's disease
TCA: Tricarboxylic acid cycle
ADD: Attention deficit disorder
ADHD: Attention deficit hyperactive disorder
TBI: Traumatic brain injury
CD: Cognitive disability/dysfunction
AGEs: Advanced glycation end products
NMDA: N-methyl-D-aspartate
MDD: Major depressive disorders
TRD: Treatment-resistant depression

BRIEF DESCRIPTION OF THE DRAWINGS

FIG. 1 illustrates effect of test substances on cellular ATP levels in HepG2 cells; G1-Normal Control, G2-Positive Control ($H_2O_2$-20 μM), G3-Reference ATP (1.5 mg), G4-ALCAR (5 mg), G5-MgAT (0.005 mg), G6-ALCAR+ MgAT (5 mg+0.025 mg) (1:0.005), G7-ALCAR+MgAT (5 mg+0.05 mg) (1:0.01), G8-ALCAR+MgAT (1 mg+1 mg) (1:1)

DETAILED DESCRIPTION

The invention will now be described in detail in connection with certain preferred and optional embodiments, so that various aspects thereof may be more fully interpreted and comprehended. However, any skilled person or artisan will appreciate the extent to which such embodiments could be generalized in practice.

It is further to be understood that all terminology used herein is for the purpose of describing particular embodiments only and is not intended to be limiting in any manner or scope. Unless defined otherwise, all technical and scientific expressions used herein have the same meaning as commonly understood by one of ordinary skill in the art to which embodiments of the invention pertain.

In describing and claiming the embodiments of the present invention, the following terminology will be used in accordance with the definitions set out below which are known in the state of art.

The singular forms "a," "an," and "the" include plural references unless the context clearly dictates otherwise. Also, the term "composition" does not limit the scope of the invention for multiple compositions that can be illustrated for best mode of the invention.

The term "pharmaceutically/nutraceutically acceptable salt", as use herein, represents those salts which are within the scope of sound medical judgment, suitable for use in contact with the tissues of humans and animals without undue toxicity, irritation, allergic response and the like and commensurate with a reasonable benefit/risk ratio.

Particularly the term "pharmaceutically acceptable salts" refers to the relatively non-toxic, inorganic and organic acid addition salts of compounds, amino acid salt, sugar-based salt, alkali or alkaline earth metal salts, as well as solvates, co-crystals, polymorphs and the like of the salts.

All modifications and substitutions that come within the meaning of the description and the range of their legal equivalents are to be embraced within their scope. A description using the transition "comprising" allows the inclusion of other elements to be within the scope of the invention.

In preferred embodiment, the invention provides synergistic compositions comprising specific combination of acetyl-L-carnitine (ALCAR) and magnesium acetyl taurate (MgAT) which are present in specific weight ratio along with pharmaceutically acceptable excipients. In another embodiment, the invention provides synergistic composition for improving physical and mental fatigue.

The term "cellular fatigue" refers to a form of fatigue that originates at the cellular level, inside an organelle called the mitochondria, all cell function and physiology depend on the health of the mitochondria.

Fatigue & depressive symptoms are very commonly seen in neurological disorders more than 80% patients of Multiple sclerosis & stroke (post stroke syndrome) complain of fatigue & depressive symptoms. Fatigue interferes with patients' activities of daily living, has a remarkable negative impact on quality of life but sadly fatigue is one of the most ignored symptoms in neurology.

The present composition is composed of synergistic combination of acetyl-L-carnitine (ALCAR) and magnesium acetyl taurate (MgAT), which are present in a therapeutically effective amount. The composition exhibits significant anti-fatigue effect with enhanced bioavailability, solubility, and therapeutic efficacy.

In another embodiment, the invention provides compositions comprising combination of therapeutically effective amount of ALCAR and MgAT in specific ratio, along with pharmaceutically acceptable excipients, wherein ALCAR moiety improves ATP production by regulating Kreb's cycle and simultaneously or concomitantly MgAT increases intracellular Mg concentration for ATP binding. The composition provides synergistic effect by ameliorating production and stabilization of ATP.

In another embodiment the invention provides synergistic compositions comprising combination of acetylating agent and NMDA antagonist along with pharmaceutically acceptable excipients for treating major depressive disorders (MDD) and/or treatment-resistant depression (TRD).

Acetyl-L-carnitine (ALCAR) is also known as ALC, is an acetylated form of L-carnitine, (3R)-3-acetyloxy-4-(trimethylazaniumyl) butanoate. It has molecular formula $C_9H_{17}NO_4$, represented below as Formula I.

ALCAR represents a major, natural supplement for combating tiredness or exhaustion. ALCAR can easily pass blood-brain barrier and reach the brain and nerves, where it can improve cellular function. Additionally, ALCAR can supply acetyl groups for the synthesis of acetyl-CoA. ALCAR also can shuttle fatty acids into mitochondria for beta-oxidation.

Acetylcholine is the neurotransmitter needed by the neurons of the brain to communicate with each other. Low acetylcholine causes difficulties with cognition, "brain fog", and mental fatigue.

Acetylcholine is required by the peripheral nervous system allowing muscles to work. Insufficient acetylcholine levels result in muscle weakness that worsen with exercise or exertion. The muscles may work for a while, then exhaust their supply of acetylcholine, leading to extreme fatigue. Thus, the reductions in plasma choline associated with strenuous exercise may reduce acetylcholine release and could thereby affect endurance or performance.

ALCAR can provide an acetyl moiety that can be oxidized for energy, used as a precursor for acetylcholine. Acetyl COA is the "feeding" molecule for the citric acid cycle.

In another embodiment, the therapeutically active moiety ALCAR restores normal mitochondrial function by maintaining the equilibrium between acyl-CoA and free CoA, it enhances fatty acid metabolism in the mitochondria and reverses the age-related decline in carnitine levels and improves β-oxidation.

Further it is a significant source of acetyl group, and hence facilitates entry of the intermediary metabolites into the Krebs cycle.

In another embodiment the administration of effective amount of ALCAR improves ATP production, reduces oxidative stress and mitochondrial alterations, and alleviates mitochondrial dysfunction and apoptosis.

It further increases L-Carnitine's hydrophobicity, which permits ALC's crossing of the blood-brain barrier.

In another embodiment, the invention provides synergistic composition comprising a therapeutically effective amount of ALCAR along with pharmaceutically acceptable salts thereof, wherein ALCAR is present in the range of 1-1000 mg, preferably in the range of 1-500 mg of total composition.

In another embodiment, the invention provides the bioactive combination, wherein the synergistic effect for stabilizing ATP is achieved by increasing intracellular $Mg^{2+}$ concentration through MgAT.

Magnesium acetyl taurate (MgAT) also may be referred to as Magnesium acetyl taurate dehydrate, chemically known as magnesium; 2-acetamidoethanesulfonate; dihydrate. It has chemical formula $C_8H_{20}MgN_2O_{10}S_2$ depicted below as Formula II.

Formula I

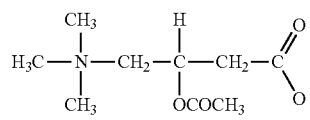

Acetyl-L-Carnitine (ALCAR) is an acetylated form of L-carnitine or it is an ester of the trimethylated amino acid L-carnitine. The major difference between acetyl-carnitine and carnitine is that acetyl-carnitine is more easily absorbed from the gut, and more readily crosses the blood-brain barrier. ALCAR is also a more easily bioavailable molecule.

Formula II

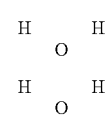

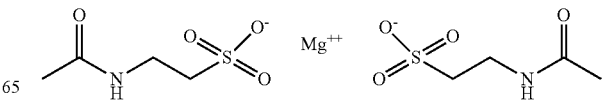

Magnesium acetyl taurate is rapidly absorbed and is able to pass Mg through cellular membrane. Magnesium is an element of great importance functioning because of its association with many cellular physiological functions.

The intracellular ATP and $Mg^{2+}$ form Mg-ATP complexes,—since both ATP and $Mg^{2+}$ are mutually and strongly buffered in cytosol. $Mg^{2+}$ deeply contributes to energy metabolism.

In another embodiment the invention provides synergistic combination where MgAT regulates mitochondrial $Mg^{2+}$ homeostasis, thereby improving TCA cycle turnover. It reduces homeostatic malfunction of mitochondrial $Mg^{2+}$.

In another embodiment, the invention provides synergistic combinations of ALCAR and MgAT, where MgAT provides free $Mg^{2+}$ for ATP binding or buffering to obtain high energy unit in the form of stabilized Mg-ATP.

Magnesium binds to ATP and causes it to change shape so that hydrolysis can take place and energy can be released into the cell, moreover Mg-ATP on hydrolysis gives energy and ADP. MgATP is the substrate of numerous phosphorylating enzymes and the principal energy source of the cell. It keeps the energy levels stable and prevents the onset of fatigue.

In another embodiment, the invention provides composition where MgAT allows more release of $Mg^{2+}$ in cytosol. $Mg^{2+}$ released in the cytosol binds to the cytosolic free ATP, thereby favoring the export of free ATP from mitochondria.

In another embodiment, the invention provides synergistic combination of ALCAR and MgAT, where MgAT provides free $Mg^{2+}$ for ATP binding or buffering to obtain high energy unit in the form of Mg-ATP.

Further Mg ion from MgAT salt blocks the ion channel of the NMDA receptor and prevents excessive activation. Moreover, administration of MgAT either in combination with acetylating agent or NMDA antagonist acts synergistically on depression or anxiety related symptoms in the subject in need thereof.

Particularly, the term "elemental magnesium" as used in connection with a magnesium-counter-ion compound described herein, may refer to a total amount of magnesium that is present as free ion and magnesium that is bound with one or more counter ions.

In yet another embodiment, the present invention provides synergistic compositions comprising therapeutically effective amount of MgAT along with pharmaceutically acceptable salts thereof, wherein MgAT is present in the range of 1-1000 mg, wherein elemental $Mg^{2+}$ is present in the range of 1-250 mg of total composition.

In one additional embodiment, the present invention provides synergistic compositions comprising magnesium acetyl taurate comprising 6 to 9% w/w of elemental magnesium by weight of total magnesium acetyl taurate. More particularly 1 mg to 1000 mg unit dose of magnesium salt of acetyl taurate containing 1 mg to 100 mg of elemental magnesium.

In another embodiment, the invention provides synergistic compositions wherein the composition comprises a therapeutically active exogenous blend of ALCAR and MgAT present in a suitable weight ratio, along with pharmaceutically acceptable excipients.

In another preferred embodiment, the invention provides novel anti-fatigue compositions comprising synergistic combinations of effective amount of ALCAR and MgAT along with pharmaceutically acceptable excipients.

In another preferred embodiment the invention provides a synergistic composition comprising therapeutically active exogenous combination of an effective amount ALCAR and MgAT which are present in the weight ratio of 1:0.002 to 1:1 along with pharmaceutically acceptable excipients.

In yet another preferred embodiment, the invention provides bioactive compositions for ameliorating cellular energy comprising exogenous blend of therapeutically active ALCAR and MgAT present in the weight ratio of 1:0.002 to 1:1, along with pharmaceutically acceptable excipients, wherein the theses two active ingredients act synergistically to improve cellular energy.

In yet another preferred embodiment, the invention provides compositions for potentiating stabilized ATP comprising exogenous blend of therapeutically active ALCAR and MgAT which are present in weight ratio of 1:0.002 to 1:1, along with pharmaceutically acceptable excipients, wherein the ALCAR improves the fatty acid metabolism and activates acetyl COA as a precursor for Kreb's cycle and acetylcholine; concurrently MgAT provides intracellular free $Mg^{2+}$ for ATP stabilization.

In one more embodiment, the invention provides composition comprising ALCAR present in a range of 50% to 99% by weight of the total composition.

In another embodiment, the invention provides composition comprising MgAT which is present in a range of 1% to 50% by weight of the total composition.

In another embodiment, the invention provides synergistic bioactive composition useful for improving cellular energy.

In one embodiment, the present invention provides synergistic composition, wherein ALCAR produces ATP which binds to magnesium ion ($Mg^{2+}$) of MgAT to compose biologically functional form i.e. Mg-ATP complexes. Because both ATP and $Mg^{2+}$ are mutually and strongly buffered in cytosol, $Mg^{2+}$ deeply contributes on energy metabolism.

In yet another embodiment the invention provides the synergistic composition comprising therapeutically active exogenous combination of effective amount ALCAR and MgAT which are present in the weight ratio of 1:0.002 to 1:1 along with pharmaceutically acceptable excipients, which improves the ATP level by 65 to 575 folds over the baseline.

In one further embodiment the invention provides the synergistic composition comprising therapeutically active exogenous blend of effective amount ALCAR and MgAT which are present in the weight ratio of 1:0.005 along with pharmaceutically acceptable excipients, which improves the ATP level by 66.76% over the normal cell control.

In one further embodiment the invention provides the synergistic composition comprising therapeutically active exogenous blend of effective amount ALCAR and MgAT which are present in the weight ratio of 1:0.01 along with pharmaceutically acceptable excipients, which improves the ATP level by 143.54% over the normal cell control.

In one further embodiment the invention provides the synergistic composition comprising therapeutically active exogenous blend of effective amount ALCAR and MgAT which are present in the weight ratio of 1:1 along with pharmaceutically acceptable excipients, which improves the ATP level by 572.51% over the normal cell control.

In one embodiment the invention provides an anti-fatigue bioactive composition with stabilized ATP comprising an exogenous blend of acetyl L-carnitine and magnesium acetyl taurate in a weight ratio of 1:0.002 to 1:1, along with pharmaceutically acceptable excipients.

In another embodiment the invention provides anti-fatigue bioactive composition for treating cellular fatigue.

In another embodiment the invention provides anti-fatigue bioactive composition wherein the stabilized ATP level is 65 to 575 folds higher than the normal cell control.

In another embodiment the invention provides anti-fatigue bioactive composition wherein the composition is orally administered with effective unit dose of 10 mg to 1000 mg.

The term "therapeutically effective amount" denotes an amount that reduces the risk, potential, possibility or occurrence of a disease or disorder, or provides advanced alleviation, mitigation, and/or reduction or restoration or modulation, regulation of at least one indicator/biomarker (e.g., blood or serum CRP level), and/or minimize at least one clinical symptom related to ATP depletion.

The term "subject in need thereof" pertains to a subject preferably mammal, more preferably human suffering or suspected with fatigue conditions.

In the context of the present invention, the term "treatment" relates to alleviating, mitigating, prophylaxis, attenuating, managing, regulating, modulating, controlling, minimizing, lessening, decreasing, down regulating, up regulating, moderating, inhibiting, restoring, suppressing, reversing, limiting, blocking, preventing, stabilizing, ameliorating, or curing, healing.

In another embodiment, the invention provides therapeutic composition that facilitates in transport of fatty acids to mitochondria for their beta-oxidation & thereby energy production.

The composition easily crosses blood brain barrier & improves mitochondrial function the brain cells. Further it significantly increases energy product, thereby improves fatigue, anxiety & depressive symptoms.

Notably, the present synergistic composition is non-hazardous, non-toxic, food ingredient and safe for human consumption without any adverse effects, therefore the present nutritional composition can also be used under preventive therapy/adjuvant therapy/add-on therapy/combination/adjunctive therapy in a subject in need thereof.

Certain compounds of the present invention can exist in unsolvated forms as well as solvated forms, including hydrated forms. Further some compounds of the present invention can exist in multiple crystalline or amorphous forms ("polymorphs"). Compounds of the invention can also exist in geometric or enantiomeric or stereoisomeric forms.

As used herein, the term "pharmaceutically acceptable carriers, diluents or excipients" is purported to mean, without limitation, any adjuvant, carrier, excipient, sweetening agent, diluents, preservative, dye/colorant, flavor enhancer, surfactant, wetting agent, dispersing agent, suspending agent, stabilizer, isotonic agent, solvent, emulsifier, or encapsulating agent, encapsulating polymeric delivery systems or polyethyleneglycolMgATrix, which is acceptable for use in the subject, preferably humans. Excipients may also include, for example: antiadherents, antioxidants, binders, coatings, compression aids, disintegrants, dyes (colors), emollients, emulsifiers, fillers (diluents), film formers or coatings, fragrances, glidants (flow enhancers), lubricants, preservatives, sorbents, suspending or dispersing agents, sweeteners, surfactant, anticaking agent, food additives, or waters of hydration, salts.

In another embodiment, the invention relates to synergistic compositions, which can be prepared in a manner well known in the pharmaceutical art, and can be administered by a variety of routes, depending upon whether local or systemic treatment is desired and upon the area to be treated. The preferable route of administration includes but not limited to sublingual, rectal, topical, parenteral, nasal, or oral.

In some embodiment, the present synergistic medicinal composition can be administered to the subject in need thereof, in the form which is suitable for oral use, such as a tablet, capsule (in the form of delayed release, extended release, sustained release, enteric coated release); hard gelatin capsules, soft gelatin capsules in an oily vehicle, veg capsule, hard or soft cellulose capsule, granulate for sublingual use, effervescent or carbon tablets, aqueous or oily solution, suspension or emulsion, encapsulate, matrix, coat, beadlets, nanoparticles, caplet, granule, particulate, agglomerate, spansule, chewable tablet, lozenge, troche, solution, suspension, rapidly dissolving film, elixir, gel, tablets, pellets, granules, capsules, lozenges, aqueous or oily solutions, suspensions, emulsions, sprays or reconstituted dry powdered form with a liquid medium or syrup; for topical use including transmucosal and transdermal use, such as a cream, ointment, gel, aqueous or oil solution or suspension, salve, parch or plaster; for nasal use, such as a snuff nasal spray or nasal drops; for vaginal or rectal use, such as a suppository; for administration by inhalation, such as a finely divided powder or a liquid aerosol; for sub-lingual or buccal use, such as a tablet, capsule, film, spray. Further, the composition can be formulated for parenteral use including intravenous, subcutaneous, intramuscular, intravascular, infusion, intraperitoneal, intracerebral, intracerebroventricular, or intradermal.

Formulations of the present invention suitable for oral administration can be presented as discrete units such as capsules (e.g., soft-gel capsules), cachets or tablets each containing a predetermined amount of the active ingredient; as a powder or granules; as a solution or a suspension in an aqueous liquid or a non-aqueous liquid, syrup; or as an oil-in-water liquid emulsion or a water-in-oil liquid emulsion. The active ingredients can also be presented in the form of a bolus, electuary or paste, nutritional bar, energy bars (candy bars), powder, granule sachet.

Further, the present composition can be formulated in the form of age-appropriate pediatric oral dosage forms such as syrup, minitablets, chewable formulations, orodispersible films, orodispersible tablets and bioadhesive buccal tablets. It can also be prepared in the form of snack, chocolate bars or other confectionery food products.

In another embodiment, the synergistic composition of the present invention is non-toxic, cost effective, enriched with bioactive ingredients, and provides safeguard against problems associated with ATP deficiency without any adverse effect.

In another embodiment of the invention, the diluents are selected from starches, hydrolyzed starches, partially pregelatinized starches, anhydrous lactose, cellulose powder, lactose monohydrate, sugar alcohols such as sorbitol, xylitol and mannitol, silicified microcrystalline cellulose, ammonium alginate, calcium carbonate, calcium lactate, dibasic calcium phosphate (anhydrous/dibasic dehydrate/tribasic), calcium silicate, calcium sulphate, cellulose acetate, corn starch, pregelatinized starch, dextrin, β-cyclodextrin, methylated-β-cyclodextrin, dextrates, dextrose, erythritol, ethyl cellulose, fructose, fumaric acid, glyceryl palmitostearate, magnesium carbonate, magnesium oxide, maltodextrin, maltose, medium-chain triglycerides, polydextrose, polymethacrylates, sodium alginate, sodium chloride, sterilizable maize, sucrose, sugar spheres, talc, trehalose, xylitol, vehicles like petrolatum, dimethyl sulfoxide and mineral oil or the like.

In some embodiment of the invention, the diluent in the composition/formulation is present in a range of 1% to 30% by weight of the total composition/formulation.

In yet another embodiment of the invention, the binder is selected from disaccharides such as sucrose, lactose, polysaccharides and their derivatives like starches, cellulose, or modified cellulose such as microcrystalline cellulose and cellulose ethers such as hydroxypropyl cellulose (HPC); hydroxypropyl methyl cellulose (HPMC); sugar alcohols such as xylitol, sorbitol, or mannitol; protein like gelatin; synthetic polymers such as polyvinylpyrrolidone (PVP), polyethylene glycol (PEG), starch, acacia, agar, alginic acid, calcium carbonate, calcium lactate, carbomers, carboxymethylcellulose sodium, carrageenan, cellulose acetate phthalate, chitosan, co-povidone, corn starch, pregelatinized starch, cottonseed oil, dextrates, dextrin, dextrose, ethyl cellulose, guar gum, hydrogenated vegetable oil, mineral oil, hydroxyethyl cellulose, hydroxymethyl cellulose, hydroxyl ethyl methyl cellulose, hydroxypropyl cellulose, inulin, cellulose, methyl cellulose, polyvinylpyrrolidone and polyethylene glycol, lactose, liquid glucose, hypromellose, magnesium aluminum silicate, maltodextrin, maltose, methylcellulose, microcrystalline cellulose, pectin, poloxamer, polydextrose, polymethacrylates, povidone, sodium alginate, stearic acid, sucrose, sunflower oil, various animal vegetable oils, and white soft paraffin, paraffin, flavorants, colorants and wax.

In further embodiment of the invention, the binder in the composition/formulation is present in a range of 0.1 to 40% by weight of the composition/formulation.

In some embodiment, the antioxidant is selected from tocopherol (vitamin E), sesamol, guaiac resin, mehionine, beta-carotene, lycopene, lutein, zeaxanthin, butylated hydroxyanisole (BHA), butylated hydroxytoluene (BHT), sodium ascorbate, sodium metabisulfite (SMB), l-carnosine, propyl gallate (PG), tertiary butyl hydroquinone, cysteine (CYS), citric acid, tartaric acid, phosphoric acid and ascorbic acid.

In some embodiment of the invention, the amount of antioxidant in the composition/formulation is present in the range of 0.1 to 10% by wt. of the composition/formulation.

In another embodiment of the invention, the lubricant is selected from magnesium stearate, zinc stearate, calcium stearate, glycerin monostearate, glyceryl behenate, glyceryl palmitostearate, hydrogenated castor oil, hydrogenated vegetable oil, light mineral oil, magnesium lauryl sulphate, medium-chain triglycerides, mineral oil, myristic acid, palmitic acid, poloxamer, polyethylene glycol, sodium benzoate, sodium chloride, sodium lauryl sulphate, sodium stearyl fumarate, stearic acid, talc, potassium, or sodium benzoate or the like.

In some embodiment of the invention, the lubricant in the composition/formulation is present in a range of 0.1% to 10.0% by weight of the total composition/formulation.

In another embodiment of the invention, the solubilizing agent is selected from polysorbate 80, sodium lauryl sulphate, anionic emulsifying wax, nonionic emulsifying wax, glyceryl monooleate, phospholipids, polyoxyethylene alkyl ethers, polyoxyethylene castor oil derivatives, polyoxyethylene sorbitan fatty acid esters, polyoxyethylene stearates, polyoxylglycerides, sorbitan esters, triethyl citrate, vitamin E, polyethylene glycol succinate, microcrystalline cellulose, carboxymethylcellulose sodium, diethanolamine, ethylene glycol palmitostearate, glycerin monostearate, hypromellose, hypromellose, acetate succinate, lecithin, polyethylene alkyl ethers, aluminum oxide, poly(methylvinyl ether/maleic anhydride), calcium carbonate, crospovidone, cyclodextrins, fructose, hydroxypropyl betadex, oleyl alcohol, povidone, benzalkonium chloride, benzethonium chloride, benzyl alcohol, benzyl benzoate, cetylpyridinium chloride, inulin, meglumine, poloxamer, pyrrolidone, sodium bicarbonate, starch, stearic acid, sulfobutylether beta cyclodextrin, tricaprylin, triolein, docusate sodium, glycine, alcohol, self-emulsifying glyceryl monooleate, cationic benzethonium chloride, cetrimide, xanthan gum, lauric acid, myristyl alcohol, butylparaben, ethylparaben, methylparaben, propylparaben, sorbic acid or the like.

In another embodiment of the invention, the amount of solubilizing agent or surfactant in the composition/formulation ranges from 0.1% to 10% by weight of the composition/formulation.

In a preferred embodiment of the invention, the solubilizing agent or surfactant is present in a range of 0.1% to 5.0% by weight of the composition/formulation.

In some embodiment of the invention, the glidant is selected from colloidal silicon dioxide, magnesium stearate, fumed silica (colloidal silicon dioxide), starch, talc, calcium phosphate tribasic, cellulose powdered, hydrophobic colloidal silica, magnesium oxide, zinc stearate, magnesium silicate, magnesium trisilicate, silicon dioxide or the like.

In another embodiment of the invention, the glidant in the composition/formulation is present in a range of 0.1% to 5.0% by weight of the total composition/formulation.

In some embodiment of the invention, the stabilizers are selected from the group consisting of alginate, agar, carrageen, gelatin, guar gum, gum arabic, locust bean gum, pectin, starch, xanthan gum, trehalose and likewise.

In some embodiment of the invention, the stabilizer in the composition/formulation is present in a range of 0.1% to 10.0% by weight of the total composition/formulation. In some embodiment of the invention, the plasticizers are added to coating formulations selected from the group propylene glycol, glycerol, glyceryl triacetate (triacetin), triethyl citrate, acetyl triethyl citrate, diethyl phthalate, actetylated monoglycerides, castor oil, mineral oil and like thereof.

In some embodiment of the invention, the plasticizer in the composition/formulation is present in a range of 0.1% to 5.0% by weight of the total composition/formulation.

In some embodiment of the invention, the solvent is selected from water, alcohol, isopropyl 10 alcohol, propylene glycol, mineral oil, benzyl alcohol, benzyl benzoate, flavored glycol, carbon dioxide, castor oil, corn oil (maize), cottonseed oil, dimethyl ether, albumin, dimethylacetamide, ethyl acetate, ethyl lactate, medium-chain triglycerides, methyl lactate, olive oil, peanut oil, polyethylene glycol, polyoxyl, castor oil, propylene carbonate, pyrrolidone, safflower oil, sesame oil, soybean oil, sunflower oil, water-miscible solvents, organic polar or non-polar solvents or mixtures thereof.

In a preferred embodiment of the invention, the solvent in the composition/formulation is used in a quantity sufficient to make the weight of the composition/formulation 100% by weight. The additional additives include a polymer, a plasticizer, a sweetener, and a powdered flavor, a preservative, a colorant, a surfactant, and other excipients. The powdered flavor composition includes a flavourant associated with a solid carrier. Coating materials such as synthetic polymers, shellac, corn protein (zein) or other polysaccharides, gelatin, fatty acids, waxes, shellac, plastics, and plant fibers and like thereof are used.

In a preferred embodiment of the invention, the additives are used in a range of 1 to 20% w/w of unit dose.

In yet another embodiment, the invention provides the synergistic composition comprising a therapeutic blend of ALCAR and MgAT along with pharmaceutical excipients, wherein the pharmaceutical excipients are selected from a diluent, a binder, a lubricant, a glidant, an additive, a surfactant, a stabilizer or mixtures thereof.

In a preferred embodiment, the invention provides the composition wherein the pharmaceutically acceptable excipients are selected from a group consisting of the diluent is present in a range of 1 to 30%; the binder present is present in a range of 0.5 to 25%; the lubricant is present in a range of 0.1 to 10.0%; the glidant is present in a range of 0.1 to 5.0%; the additive is present in a range of 1 to 10%; the surfactant is present in a range of 0.1 to 5.0%; the stabilizer is present in a range of 0.1 to 5.0%; %; the antioxidant is present in a range of 0.1 to 5.0%; and the plasticizer is present in a range of 0.1 to 5.0%; by weight of total composition.

In further embodiment compositions containing compounds of the invention, can be conveniently presented in unit dosage form and prepared by any of the methods well known in the art of pharmacy. Preferred unit dosage formulations are those containing an effective dose, or an appropriate fraction thereof, of the active ingredient, or a pharmaceutically acceptable salt thereof. The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose (in single or divided doses) ranges from about 1 mg per day to about 2500 mg per day, preferably about 10 mg per day to about 1000 mg per day.

In another embodiment, the present invention provides a method for potentiating stabilized ATP in a subject in need thereof. The method comprises administering an oral dose of a therapeutically effective amount of a medicinal composition comprising an exogenous synergistic combination of acetyl L-carnitine and magnesium acetyl taurate, wherein acetyl L-carnitine and magnesium acetyl taurate are present in a weight ratio of: 0.002 to 1:1, along with pharmaceutically acceptable excipients.

In certain embodiments, the invention provides the potent composition wherein the effective unit dose for an oral administration is formulated in a range of 10 to 1000 mg.

It is further recommended that children, patients over 60 years old, initially receive low doses and that the dosage be titrated based on individual physiological responses and/or pharmacokinetics. It can be necessary to use dosages outside these ranges in some cases, as will be apparent to those in the art. The present composition can be used as infant formula as well as adult formula by varying the concentration of active ingredients. Further, it is noted that the dietician or nutritionist or certified physician knows how and when to interrupt, adjust or terminate therapy in conjunction with an individual patient's response.

The use of any and all examples, or exemplary language (e.g., such as) provided herein, is intended merely to better illuminate the invention, and does not pose a limitation on the scope of the invention unless otherwise claimed.

Various other examples of compositions and modifications or adaptations thereof can be devised by a person skilled in the art after reading the foregoing preferred embodiments without departing from the spirit and scope of the invention. All such further examples, modifications and adaptations are included within the scope of the invention.

It will be appreciated by those versed in the art that the present invention makes available novel and useful nutraceutical compositions and nutraceutical acceptable salts thereof, which have neuroprotective effects in several administration forms. Also, it will be understood by those with knowledge in the dietary supplement and nutraceutical art, that many embodiments of this invention may be made without departing from the spirit and scope of the invention, and the invention is not to be construed as limited, as it embraces all equivalents therein.

The invention may be further illustrated by the following examples, which are for illustrative purposes only and should not be construed as limiting the scope of the invention in anyway.

The present disclosure is therefore to be considered as in all respects illustrative and not restrictive, the scope of the invention being indicated by the appended claims and examples, and all changes or alterations which come within the ambit of equivalency are intended to be encompassed therein.

EXAMPLES

Having described the basic aspects of the present invention, the following non-limiting examples illustrate specific embodiments thereof. Those skilled in the art will appreciate that many modifications may be made in the invention without changing the essence of invention.

Example—1 i. Composition 1: Synergistic Blend

| Ingredient | w/w % |
| --- | --- |
| ALCAR | 50 to 99% |
| MgAT | 1% to 50% | ii. Composition 2: Tablet/Capsule

| Ingredient | w/w % unit dose |
| --- | --- |
| ALCAR | 50 to 99% |
| MgAT | 1 to 50% |
| Excipient | 5-20% |
| Average Weight | 100% | iii. Composition 3: Tablet/Capsule

| Ingredient | w/w % unit dose |
| --- | --- |
| ALCAR | 50-99% |
| MgAT | 1-50% |
| Diluents | 1-10% |
| Binders | 0.5-5% |
| Glidants | 0.5-5% |
| Lubricants | 0.5-5% |
| Stabilizers | 0.1-10% | iv. Composition 4: Tablet/Capsule

| Ingredient | w/w % unit dose |
| --- | --- |
| Additives | 1-10% |
| Antioxidant | 0.1-5% |
| Solvents | QS |

| Ingredient | mg per unit dose |
| --- | --- |
| ALCAR | 500 |
| MgAT | 5 |
| Sodium Benzoate | 1-5 |
| Magnesium Stearate | 1-10 |
| Hydroxypropyl Methylcellulose | 1-10 |
| Microcrystalline Cellulose | 1-20 |
| PVP K-30 | 5-10 |
| Silicon dioxide | 1-10 |
| Polysorbate 20 | 1-10 |
| Sorbitol | 1-20 |
| Propylene Glycol | QS |
| Water | QS |
| Average weight | 510-600 mg | v. Composition 5: Tablet/Capsule

| Ingredient | mg per unit dose |
| --- | --- |
| ALCAR | 500 |
| MgAT | 1 |
| Sodium Benzoate | 1-10 |
| Magnesium Stearate | 1-20 |
| Sodium ascorbate | 2-10 |
| Microcrystalline Cellulose | 2-20 |
| Colloidal Silicon dioxide | 5-15 |
| Hydroxypropyl Methylcellulose | 2-10 |
| triethyl citrate | 2-10 |
| PVP K-30 | 5-10 |
| Talc | 1-10 |
| Tween 80 | 1-10 |
| Mannitol | 5-20 |
| Alcohol | QS |
| Water | QS |
| Average weight | 500-560 mg | vi. Composition 6: Tablet/Capsule

| Ingredient | mg per unit dose |
| --- | --- |
| ALCAR | 500 |
| MgAT | 2.5 |
| Sodium Benzoate | 1-5 |
| Microcrystalline Cellulose | 2-20 |
| Silicon dioxide | 1-10 |
| Hydroxypropyl Methylcellulose | 2-10 |
| Stearic acid | 2-10 |
| Dibasic calcium phosphate | 1-20 |
| Pregelatinized starch | 5-10 |
| Talc | 1-10 |
| Tween 80 | 1-10 |
| polydextrose | 1-10 |
| Water | QS |
| Average weight | 500-550 mg | vii. Composition 7: Tablet/Capsule

| Ingredient | mg per unit dose |
| --- | --- |
| ALCAR | 250 |
| MgAT | 25 |
| Microcrystalline Cellulose | 1-10 |
| Silicon dioxide | 1-10 |
| Ethyl Cellulose | 1-10 |
| Hydroxypropyl Methylcellulose | 1-10 |
| Magnesium Stearate | 2-10 |
| Polyvinylpyrrolidone | 1-10 |
| Talc | 1-10 |
| Polysorbate 20 | 1-10 |
| Mannitol | 1-10 |
| IPA | QS |
| Water | QS |
| Average weight | 280-330 mg | viii. Composition 8: Tablet/Capsule

| Ingredient | mg per unit dose |
| --- | --- |
| ALCAR | 200 |
| MgAT | 50 |
| Silicon Dioxide | 1-10 |
| Medium-chain triglycerides | 1-5 |
| Microcrystalline Cellulose | 2-20 |
| Dibasic Calcium Phosphate | 2-20 |
| Magnesium Stearate | 2-10 |
| Croscarmellose sodium | 2-10 |
| Polyvinylpyrrolidone | 1-20 |
| Talc | 1-10 |
| Corn Starch | 1-10 |
| Sodium ascorbate | 1-10 |
| Propylene glycol | 1-10 |
| Water | QS |
| Average weight | 255-300 mg | ix. Composition 9: Tablet/Capsule

| Ingredient | mg per unit dose |
| --- | --- |
| ALCAR | 100 |
| MgAT | 100 |
| Microcrystalline Cellulose | 1-10 |
| Colloidal silicon dioxide | 1-10 |
| Hydroxypropyl Methylcellulose | 1-10 |
| Magnesium Stearate | 2-10 |
| Polyvinylpyrrolidone | 1-10 |
| Calcium Phosphate | 1-10 |
| Ascorbic Acid | 1-10 |
| Polysorbate 20 | 1-10 |
| Talc | 1-5 |
| Sucrose | 1-10 |
| Mannitol | 1-10 |
| Glycerol | 1-10 |
| Average weight | 250-350 mg | x. Composition 10: Tablet/Capsule

| Ingredient | mg per unit dose |
| --- | --- |
| ALCAR | 200 |
| MgAT | 50 |
| Microcrystalline Cellulose | 1-10 |
| Silicon dioxide | 1-10 |
| Hydroxypropyl Methylcellulose | 1-10 |
| Magnesium Stearate | 2-10 |
| Zinc Stearate | 1-5 |
| Polyvinylpyrrolidone | 1-10 |
| Mineral Oil | 1-10 |
| Sodium benzoate | 1-10 |
| Ascorbic Acid | 1-10 |
| Polysorbate 20 | 1-10 |
| Talc | 1-5 |

-continued

| Ingredient | mg per unit dose |
|---|---|
| Dextrose | 1-10 |
| Mannitol | 1-10 |
| Water | QS |
| Average weight | 250-350 mg | xi. Composition 11: Tablet/Capsule

| Ingredient | mg per unit dose |
|---|---|
| ALCAR | 200 |
| MgAT | 100 |
| Microcrystalline Cellulose | 1-10 |
| Silicon dioxide | 1-10 |
| Hydroxypropyl Methylcellulose | 1-10 |
| Magnesium Stearate | 2-10 |
| Zinc Stearate | 1-5 |
| Polyvinylpyrrolidone | 1-10 |
| Mineral Oil | 1-10 |
| Sodium benzoate | 1-10 |
| Citric Acid | 1-10 |
| Polysorbate 80 | 1-10 |
| Talc | 1-5 |
| Sucrose | 1-10 |
| Mannitol | 1-10 |
| Water | QS |
| Average weight | 320-370 mg | xii. Composition 12: Tablet/Capsule

| Ingredient | mg per unit dose |
|---|---|
| ALCAR | 500 |
| MgAT | 50 |
| Sodium Benzoate | 5 |
| Microcrystalline Cellulose | 1-10 |
| Colloidal Silicon dioxide | 1-10 |
| Hydroxypropyl cellulose | 1-10 |
| Magnesium Stearate | 2-10 |
| Calcium Stearate | 1-5 |
| Polyvinylpyrrolidone | 1-10 |
| Mineral Oil | 1-10 |
| Sodium benzoate | 1-10 |
| Ascorbic Acid | 1-10 |
| Polysorbate 20 | 1-10 |
| Talc | 1-5 |
| Dextrose | 1-10 |
| Mannitol | 1-10 |
| Water | QS |
| Average weight | 560-650 mg |

The present composition is stable for 24 months under the accelerated condition [40° C., 75% RH], where the purity of the active ingredients is above 95%.

Example 2: Animal Study

In vitro evaluation of the modulatory potential of the test substances on cellular ATP levels in (HepG2) human Hepatocellular carcinoma cell line.
Outline of the Method:
The in vitro cytotoxicity was performed on HepG2 (Human Hepatocellular Carcinoma) cell line to find the non-toxic concentrations of the test substances by MTT assay and evaluate their modulatory potential on cellular ATP levels
Preparation of Test Solution:
About 10 mg of all the test substances were dissolved separately with 1 ml DMEM-HG supplemented with 2% inactivated FBS to obtain a stock solution of 10 mg/ml concentration and sterilized by 0.22u syringe filtration. Diluted the stock to desired concentration for carrying out further studies.
Cell Line and Culture Medium:
Cell line HepG2 was procured from NCCS (National Center for Cell Sciences), Pune, and was cultured in DMEM-HG supplemented with 10% inactivated Fetal Bovine Serum (FBS), penicillin (100 IU/ml), streptomycin (100 µg/ml) and amphotericin B (5 µg/ml) in a humidified atmosphere of 5% $CO_2$ at 37° C. until confluent. The cells were dissociated with TPVG solution (0.2% trypsin, 0.02% EDTA, 0.05% glucose in PBS). The stock cultures were grown in 25 $cm^2$ culture flasks and all experiments were carried out in 96 well microtitre plates (Tarsons India Pvt. Ltd., Kolkata, India).
Cytotoxicity Studies:
The monolayer cell culture was trypsinized and the cell count was adjusted to $1.0 \times 10^5$ cells/ml using DMEM-HG containing 10% FBS. To each well of the 96 well microtitre plate, 0.1 ml of the diluted cell suspension was added. After 24 h, when a partial monolayer was formed, the supernatant was flicked off, the monolayer was washed once with medium and 100 µl of different concentrations of test substances were added. The plate was then incubated at 37° C. for 24 h in a 5% $CO_2$ atmosphere, and microscopic examination was carried out and observations were noted after 24 h time.
Mtt Assay:
After 24 h of incubation, the drug solutions in the wells were discarded and 50 µl of MTT in DPBS was added to each well. The plate was gently shaken and incubated for 3 h at 37° C. in a 5% $CO_2$ atmosphere. The supernatant was removed and 100 µl of 2-propanol was added and the plate was gently shaken to solubilize the formed formazan. The absorbance was measured using a microplate reader at a wavelength of 570 nm. The percentage growth inhibition was calculated using the standard formula. The concentration of test substances, needed to inhibit the growth of the cell by 50% i.e., CTC50 values were generated from the dose-response curves
Estimation of Cellular Respiration by Measuring Cellular ATP Levels:
HepG2 cells were trypsinized from stock culture flasks and the cell count was adjusted to $1.0 \times 10^5$ cells/ml, the cell suspension was seeded into a 96-well plate. After 24 hr, cell cultures with 70-80% confluency, cells were treated with different non-toxic concentrations of test substances. After 24 hr of treatment, the plate was washed with phosphate buffer saline. The cellular ATP levels determination was performed according to the instruction given in the kit manual (BioVision, #K354-100). At the end of the experiment, the optical density was read at 570 nm using microplate reader. From the absorbance values, the cellular ATP levels were estimated using kit protocol and the concentration of cellular ATP levels in treated groups were determined in comparison to the control groups.
Study Design:

TABLE 1

| Group. No. | Group | Dose and Treatment | Parameters Analyzed |
|---|---|---|---|
| G1 | Cell Control | No treatment | Cellular |
| G2 | Positive Control ($H_2O_2$— 20 µM) | Positive Control ($H_2O_2$— 20 µM) | ATP levels |

TABLE 1-continued

| Group. No. | Group | Dose and Treatment | Parameters Analyzed |
|---|---|---|---|
| G3 | ATP (1.5 mg) | Cells were treated with test substances | |
| G4 | N-Acetyl L carnitine (5 mg) | Cells were treated with test substances | |
| G5 | Magnesium Acetyl Taurate (0.005 mg) | Cells were treated with test substances | |
| G6 | ALCAR & MgAT (5 mg &0.025 mg) (1:0.005) | Cells were treated with test substances | |
| G7 | ALCAR & MgAT (5 mg & 0.05 mg) (1:0.01) | Cells were treated with test substances | |
| G8 | ALCAR & MgAT (1 mg & 1 mg) (1:1) | Cells were treated with test substances | |

Results

TABLE 2

Cytotoxicity properties of test substances against HepG2 cell line

| Sl. No | Name of Test Sample | Test Conc. (µg/mL) | % Cytotoxicity | CTC50 (µg/mL) |
|---|---|---|---|---|
| 1 | Magnesium Acetyl Taurate (MgAT) | 5000 | 12.166 ± 1.560 | >5000 |
| | | 4000 | 6.165 ± 2.392 | |
| | | 3000 | 3.710 ± 1.339 | |
| | | 2000 | 6.547 ± 0.482 | |
| | | 1000 | 1.364 ± 0.967 | |
| | | 500 | 1.528 ± 0.408 | |
| | | 250 | 1.746 ± 0.430 | |
| | | 125 | 1.255 ± 0.910 | |
| | | 62.5 | 1.309 ± 0.231 | |
| 2 | N-Acetyl L Carnitine (ALCAR) | 5000 | 32.570 ± 2.550 | >5000 |
| | | 4000 | 5.183 ± 2.677 | |
| | | 3000 | 3.001 ± 0.736 | |
| | | 2000 | 2.619 ± 0.964 | |
| | | 1000 | 2.455 ± 1.576 | |
| | | 500 | 1.691 ± 0.204 | |
| | | 250 | 1.309 ± 0.134 | |
| | | 125 | 0.546 ± 0.408 | |
| | | 62.5 | 0.982 ± 0.876 | |

TABLE 3

Effect of test substances on cellular ATP levels in HepG2 cells

| Group No. | Name of the test substances | Cellular ATP (nM) | Percentage enhancement of cellular ATP levels over cell control |
|---|---|---|---|
| G1 | Cell Control | 36.29 ± 0.52 | |
| G2 | Positive Control (H$_2$O$_2$— 20 µM) | 22.35 ± 0.48 | −38.40 |
| G3 | ATP (1.5 mg) | 119.88 ± 0.45 | 230.33 |
| G4 | Test I-N-Acetyl L carnitine (5 mg) | 39.92 ± 0.45 | 10.00 |
| G5 | Test II-Magnesium Acetyl Taurate (0.005 mg) | 56.28 ± 0.56 | 55.07 |
| G6 | Composition I-ALCAR: MgAT (5 mg & 0.025 mg) (1:0.005) | 60.52 ± 0.33 | 66.76 |
| G7 | Composition III-ALCAR : MgAT (5 mg & 0.05 mg) (1:0.01) | 88.38 ± 0.45 | 143.54 |
| G8 | Composition II-ALCAR: MgAT (1 mg & 1 mg) (1:1) | 244.05 ± 0.94 | 572.51 |

Discussion and Conclusion

In the current study, the effect of test compounds on cellular ATP levels was examined. Among all the group assayed, Group 8 with the composition II-ALCAR: MgAT at 1:1 ratio exhibited the highest percentage increase in the ATP levels i.e. 572.51% over the cell control. While, test group I and II substances N-Acetyl L carnitine and Magnesium Acetyl Taurate showed increased levels of cellular ATP of 10.00% and 55.07% respectively, Compositions I & II ALCAR:MgAT (1:0.005) and ALCAR: MgAT (1:0.01) showed more promising activity by increasing the cellular ATP levels by 66.76% and 143.54% respectively. Most of the test groups and composition assayed showed considerable increase in cellular ATP levels compared to the cell control (untreated).

It is concluded that the test compounds G6, G7 and G8 are good modulators in increasing the cellular ATP level. The combination in specific ratios show significant results over individual components, i.e. more than 10 to 50 times.

We claim:

1. A synergistic composition for potentiating stabilized ATP, the synergistic composition comprising:
   a therapeutically active exogenous blend consisting of acetyl L-carnitine and magnesium acetyl taurate; and
   pharmaceutically acceptable excipients,
   wherein the acetyl L-carnitine and the magnesium acetyl taurate are present in a weight ratio of 1:0.002 to 1:1.

2. The synergistic composition according to claim 1, wherein the acetyl L-carnitine is present in a range of 50% to 99% by a total weight of the composition.

3. The synergistic composition according to claim 1, wherein the magnesium acetyl taurate is present in a range of 1% to 50% by the total weight of the composition.

4. The synergistic composition according to claim 1, wherein the pharmaceutically acceptable excipients are selected from a group consisting of a diluent present in a range of 1 to 30%, a binder present in a range of 0.1 to 25%, a lubricant present in a range of 0.1 to 10.0%, a glidant present in a range of 0.1 to 5.0%, an additive present in a range of 1 to 10%, a surfactant present in a range of 0.1 to 5.0%, a stabilizer present in a range of 0.1 to 5.0%, an antioxidant present in a range of 0.1 to 5.0%, and a plasticizer present in a range of 0.1 to 5.0%, by the total weight of the composition.

5. The synergistic composition according to claim 1, wherein an administration of an effective unit dose of the synergistic composition improves ATP level by 65 to 575 folds over a normal cell control.

6. The synergistic composition according to claim 1, wherein the acetyl L-carnitine and the magnesium acetyl taurate are present in a weight ratio of 1:0.005.

7. The synergistic composition according to claim 1, wherein the acetyl L-carnitine and the magnesium acetyl taurate are present in a weight ratio of 1:0.01.

8. The synergistic composition according to claim 1, wherein the acetyl L-carnitine and the magnesium acetyl taurate are present in a weight ratio of 1:1.

9. The synergistic composition according to claim 1, wherein an oral administration of the synergistic composition improves tiredness, fatigue, weakness, cognition, memory, increase mental alertness, concentration, endurance, boost energy levels, wakefulness, conditions associated with ATP depletion, depression, or anxiety related symptoms.

10. The synergistic composition according to claim 5, wherein the effective unit dose is formulated in a range of 10 mg to 1000 mg.

* * * * *